US011217365B2

(12) United States Patent
Shi et al.

(10) Patent No.: US 11,217,365 B2
(45) Date of Patent: Jan. 4, 2022

(54) MOBILE DEDICATED CABLE FOR MEDICAL COMPUTED TOMOGRAPHY (CT) BED

(71) Applicant: Kunshan Hwatek Wires and Cable Co., Ltd, Suzhou (CN)

(72) Inventors: Jiayou Shi, Suzhou (CN); Qing Qi, Suzhou (CN)

(73) Assignee: Kunshan Hwatek Wires and Cable Co., Ltd, Suzhou (CN)

( * ) Notice: Subject to any disclaimer, the term of this patent is extended or adjusted under 35 U.S.C. 154(b) by 496 days.

(21) Appl. No.: 16/316,296

(22) PCT Filed: Nov. 21, 2017

(86) PCT No.: PCT/CN2017/111990
§ 371 (c)(1),
(2) Date: Jan. 8, 2019

(87) PCT Pub. No.: WO2019/090813
PCT Pub. Date: May 16, 2019

(65) Prior Publication Data
US 2021/0327609 A1 Oct. 21, 2021

(30) Foreign Application Priority Data
Nov. 9, 2017 (CN) ............................ 201711098756

(51) Int. Cl.
*H01B 7/02* (2006.01)
*H01B 3/44* (2006.01)
(Continued)

(52) U.S. Cl.
CPC ........... *H01B 7/0258* (2013.01); *H01B 3/445* (2013.01); *H01B 7/1875* (2013.01);
(Continued)

(58) Field of Classification Search
CPC ........ H01B 3/445; H01B 7/02; H01B 7/0258; H01B 7/1875; H01B 7/1795; H01B 7/24; H01B 11/02; H01B 11/18
(Continued)

(56) References Cited

U.S. PATENT DOCUMENTS 5,149,915 A * 9/1992 Brunker ................. H01B 11/02
174/105 R
5,491,299 A * 2/1996 Naylor .................. A61B 5/303
174/36
(Continued)

FOREIGN PATENT DOCUMENTS

CA 2916410 A1 7/2016
CN 201117328 Y 9/2008
(Continued)

*Primary Examiner* — William H. Mayo, III
(74) *Attorney, Agent, or Firm* — Erickson Kernell IP, LLC; Kent R. Erickson

(57) ABSTRACT

A mobile dedicated cable for a medical Computed Tomography (CT) bed, having an inner sheath layer, a first Teflon® belt, a signal cable layer, a second Teflon® belt, a braided layer and an outer sheath layer, which are coaxially arranged from inside to outside in sequence. The inner sheath layer has a PVC filling strip wrapped by the first Teflon® belt, and a plurality of bulletproof filaments arranged in the center of the PVC filling strip. The signal cable layer has a plurality of signal lines evenly arranged therein, each of which are circumscribed with the first Teflon® belt and the second Teflon® belt, and with two signal lines adjacent thereto.

8 Claims, 1 Drawing Sheet

(51) Int. Cl.
*H01B 11/18* (2006.01)
*H01B 7/24* (2006.01)
*H01B 7/18* (2006.01)

(52) U.S. Cl.
CPC ............. *H01B 7/1895* (2013.01); *H01B 7/24* (2013.01); *H01B 11/18* (2013.01)

(58) Field of Classification Search
USPC ............................. 174/102 R, 103, 108, 109
See application file for complete search history.

(56) References Cited

U.S. PATENT DOCUMENTS

| | | | | | |
|---|---|---|---|---|---|
| 5,530,203 | A | * | 6/1996 | Adams | H01B 9/003 174/106 R |
| 5,834,699 | A | * | 11/1998 | Buck | H01B 11/06 174/113 R |
| 5,864,094 | A | * | 1/1999 | Griffin | H01B 11/12 174/105 R |
| 6,833,506 | B2 | * | 12/2004 | Wechsler | A61B 5/303 174/113 R |
| 7,060,905 | B1 | * | 6/2006 | McMahon | H01B 11/1891 174/11 OR |
| 10,002,689 | B2 | | 6/2018 | Straniero et al. | |
| 10,297,368 | B2 | * | 5/2019 | Chen | H01B 11/20 |
| 2011/0174517 | A1 | * | 7/2011 | Al-Ali | H01B 11/1091 174/113 R |
| 2016/0196899 | A1 | | 7/2016 | Straniero et al. | |

FOREIGN PATENT DOCUMENTS

| | | | | | |
|---|---|---|---|---|---|
| CN | 203588723 | U | * | 5/2014 | H01B 7/17 |
| CN | 203588723 | U | | 5/2014 | |
| CN | 104575852 | A | | 4/2015 | |
| CN | 207474118 | U | | 6/2018 | |
| EP | 3043358 | A1 | | 7/2016 | |
| MX | 2016000216 | A | | 7/2016 | |

* cited by examiner

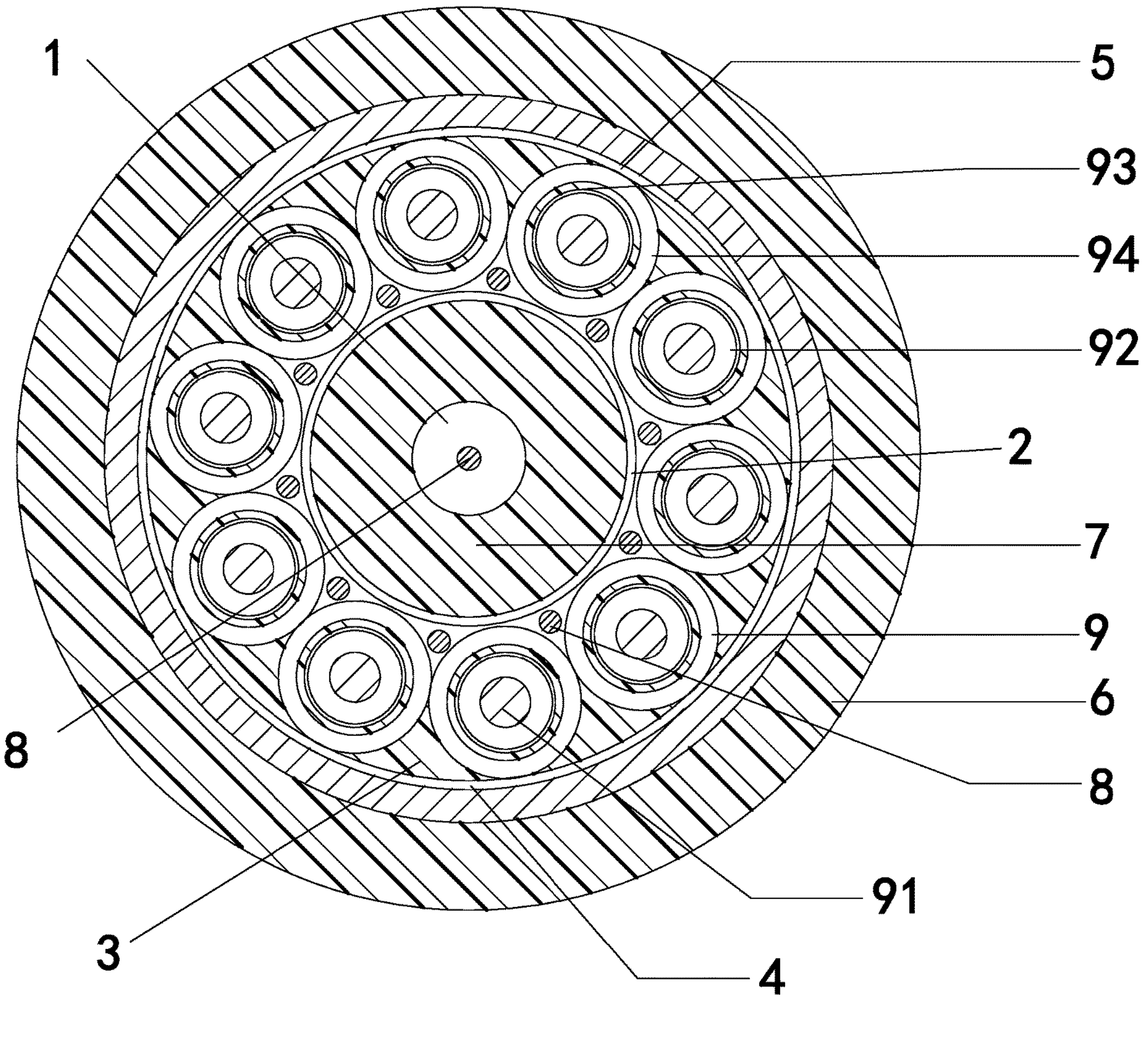
1
5
93
94
92
2
7
9
6
8
8
91
3
4

MOBILE DEDICATED CABLE FOR MEDICAL COMPUTED TOMOGRAPHY (CT) BED

CROSS-REFERENCE TO RELATED APPLICATION

This application claims priority from Chinese Patent Application No. 201711098756.4 filed Nov. 9, 2017, the contents of which are incorporated herein by this reference.

FIELD OF THE INVENTION

The present invention relates to the field of medical cable technology, and in particular, to a mobile dedicated cable for a medical computed tomography (CT) bed.

BACKGROUND OF THE INVENTION

Nowadays, people are becoming increasingly health-conscious. No matter how minor the physical problems they have are, they are willing to go to the hospital for a body check with, for example, CT scans, etc. This is not a big deal in itself, but this keeps the medical equipment working continuously. Such prolonged and frequent uses of the CT beds are not taken into account while the conventional mobile cables for the CT beds are designed and produced. The overuse may cause the machines to malfunction, delaying the patient's medical treatment, and even causing death in some serious cases.

Therefore, it is urgent to conceive a new technique to solve the above problems.

SUMMARY OF THE INVENTION

The aim of the invention is to solve the above technical problems by providing a mobile dedicated cable for a medical CT bed.

According to the invention, a mobile dedicated cable for a medical computed tomography (CT) bed comprises: an inner sheath layer, a first polytetrafluoroethylene or Teflon® belt, a signal cable layer, a second polytetrafluoroethylene or Teflon® belt, a braided layer and an outer sheath layer, which are coaxially arranged from inside to outside in sequence. The under-sheath layer comprises a PVC (polyvinyl chloride) filling strip arranged therein and wrapped with the first Teflon® belt, and a plurality of bulletproof filaments arranged in the center of the PVC filling strip. The signal cable layer comprises a plurality of signal lines which are evenly arranged therein, each of the signal lines are circumscribed with the first Teflon® belt and the second Teflon® belt, and with two signal lines adjacent thereto.

Preferably, each of the signal lines comprises a signal line conductor, a signal line insulation layer, a signal line braided layer, and a signal line sheath layer, which are coaxially arranged from inside to outside in sequence.

Preferably, the signal cable layer comprises a plurality of bulletproof filaments arranged therein.

Preferably, the outer sheath layer is a wear-resistant PVC sheath layer.

Preferably, the plurality of bulletproof filaments arranged within the PVC filling strip are 2000 denier (D) bulletproof filaments.

Preferably, the plurality of bulletproof filaments arranged within the signal cable layer are 1000 denier (D) bulletproof filaments Preferably, the signal cable layer comprises ten signal lines.

Preferably, the signal line conductor has a diameter of 1.5 mm.

With the above technical solutions, the present invention provides at least the following beneficial effects:

The mobile dedicated cable for the medical CT bed provided in the disclosure has improved flexibility and increased swing times, and is thus suitable for medical CT beds.

BRIEF DESCRIPTION OF THE DRAWINGS

FIG. 1 is a schematic view of a mobile cable dedicated for a medical CT bed according to the present invention, wherein the reference numerals associated with the parts of the mobile cable are as follows:

1. Inner sheath layer
2. First polytetrafluoroethylene belt
3. Signal cable layer
4. Second polytetrafluoroethylene belt
5. Braided layer
6. Outer sheath layer
7. PVC filling strip
8. Bulletproof filaments
9. Signal lines
10. 91. Signal line conductor
11. 92. Signal line insulation layer
12. 93. Signal line braided layer
13. 94. Signal line sheath layer.

DETAILED DESCRIPTION OF THE INVENTION

The invention will be described in detail by embodiments below with reference to the accompanying drawings. Obviously, the embodiments to be described are merely a part of embodiments of the invention, rather than all of the embodiments. All other embodiments obtained by those ordinary skilled in the art without creative effort based on the embodiments in the disclosure are within the protection scope of the present invention.

As shown in FIG. 1, according to the invention, a mobile dedicated cable for a medical CT bed comprises an inner sheath layer 1, a first polytetrafluoroethylene belt 2, a signal cable layer 3, a second polytetrafluoroethylene belt 4, a braided layer 5 and an outer sheath layer 6, which are coaxially arranged from inside to outside in sequence. The inner sheath layer 1 comprises a PVC filling strip 7 arranged therein and wrapped by the first Teflon® belt 2, and a plurality of bulletproof filaments 8 arranged in the center of the PVC filling strip 7. The PVC filler strip 7 has improved flexibility due to the plurality of bulletproof filaments 8, and the overall impact resistance performance of the cable is thus improved. The signal cable layer 3 comprises a plurality of signal lines 9 evenly arranged within, each of which are circumscribed with the first Teflon® belt 2 and the second Teflon® belt 4, and with two signal lines 9 adjacent thereto. The two Teflon® belts are configured to wrap the plurality of signal lines 9 for better overall mechanical properties for the cable.

Preferably, each of the signal lines 9 comprises a signal line conductor 91, a signal line insulation layer 92, a signal line braided layer 93, and a signal line sheath layer 94, coaxially arranged from inside to outside in sequence.

Preferably, the signal cable layer 3 also comprises a plurality of bulletproof filaments 8 arranged therein. The flexibility and the swing times of the cable can be effectively improved by the bulletproof filaments 8 added.

Preferably, the outer sheath layer 6 is a wear-resistant PVC sheath layer, and more preferably, a high flame-retardant soft wear-resistant modified PVC sheath layer. In a preferred embodiment, the sheath layer mainly comprises the following components: 70-100 parts of PVC resin, 1-10 parts of chlorinated polyethylene (CPE), 30-50 parts of ground calcium carbonate, 20-30 parts of active calcium, 8-12 parts of nano-clay, 10-20 parts of aluminum hydroxide, 40-50 parts of environment-friendly plasticizer, 5-6 parts of calcium-zinc stabilizer, 0.1-0.3 parts of stearic acid, and 0.5-1.5 parts of polyethylene (PE) wax. In a specific embodiment, the materials are prepared according to the following proportion:

PVC 100
CPE 6
ground calcium carbonate 39
active calcium 26
nano-clay 11
aluminum hydroxide 14
dioctylterephthalate 44
calcium-zinc stabilizer 5.7
stearic acid 0.2
PE-wax 1.0

By adding in CPE, the toughness and impact-resistance performances of the cable can be improved. In addition, in combination with the nano-clay, on one hand the flame retardant performance can be improved, and on the other hand the extruded cable can have higher surface strength, better friction resistance, and etc. Dioctyl phthalate which is harmful to the human body and antimony trioxide which is irritating to the skin are not used, therefore the product of the invention is more in line with environmental performance requirements.

Preferably, the bulletproof filaments 8 arranged in the PVC filling strip 7 are a 2000D Kevlar® aramid fiber.

Preferably, the bulletproof filaments 8 arranged in the signal cable layer 3 is a 1000D Kevlar® aramid fiber.

Preferably, the cable comprises ten signal lines.

Preferably, the signal line conductor 91 has a diameter of 1.5 millimeters (mm).

Preferably, the signal line conductor 91 is a silver plated compacted conductor.

According to the invention, by replacing the twisted signal lines conventionally used with the high-frequency coaxial signal lines 9, the cable has improved signal transmission, reduced signal interference which is generated by external motions, and enhanced tensile strength. In addition, the signal line conductor 91 is a silver plated compacted conductor, rather than a small pitch silver plated conductor, therefore the cable has improved flexibility. The structure of the finished cable of the invention is significantly different than the structure of conventional cables, with the center thereof comprising the high-strength PVC strip wrapped by the Teflon® belt, and the 2000D Kevlar® bulletproof filaments 8 arranged in the center of the PVC strip. Moreover, the cable comprises the plurality of bulletproof filaments 8 for improved overall mechanical performance. The number of bends in a bend test which the cable of the invention can withstand is increased to 70,000 from 30,000 which is the number of bends a conventional cable can withstand, the hoisting weight which the cable can bear is increased from 300 g to 600 g, the number of twists in a torsion test which the cable can withstand is increased from 40,000 to 120,000, and the working frequency is increased from 800 MHz to 1800 MHz. In an assembly process for the cable of the invention, a passive pay-out strand is no longer used for the assembled signal lines 9, and an active pay-out strand is used instead. In addition, the finished cable can be assembled by a cage strander instead of a single strander. The inner and outer sheath can be produced by tube extruding instead of semi-extrusion, namely an optimized process is used. The material of the sheath is changed from ordinary PVC to high flame-retardant, soft, wear-resistant modified PVC, resulting in better performance in use.

The cable of the invention is suitable for medical CT beds, its signal transmission is faster and more precise, and its compact design results in space savings. The cable of the invention has increased flexibility and swing times due to its novel structure.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. A mobile dedicated cable for a medical computed tomography (CT) bed, comprising: an inner sheath layer, a first polytetrafluoroethylene belt, a signal cable layer, a second polytetrafluoroethylene belt, a braided layer and an outer sheath layer, which are coaxially arranged from inside to outside in sequence, wherein the inner sheath layer comprises a PVC filling strip arranged therein and wrapped with the first polytetrafluoroethylene belt, and a plurality of bulletproof filaments arranged in the center of the PVC filling strip; and wherein the signal cable layer comprises a plurality of signal lines which are evenly arranged therein, each of the signal lines is circumscribed with the first polytetrafluoroethylene belt and the second polytetrafluoroethylene belt, and with two signal lines adjacent thereto.

2. The mobile dedicated cable of claim 1, wherein each of the signal lines comprises a signal line conductor, a signal line insulation layer, a signal line braided layer, and a signal line sheath layer, which are coaxially arranged from inside to outside in sequence.

3. The mobile dedicated cable of claim 2, wherein the signal line conductor has a diameter of 1.5 millimeters.

4. The mobile dedicated cable of claim 1 or 2, wherein the signal cable layer comprises a plurality of bulletproof filaments arranged therein.

5. The mobile dedicated cable of claim 4, wherein the plurality of bulletproof filaments arranged within the signal cable layer are 1000 denier bulletproof filaments.

6. The mobile dedicated cable of claim 1, wherein the outer sheath layer is a wear-resistant PVC sheath layer.

7. The mobile dedicated cable of claim 1, wherein the plurality of bulletproof filaments arranged within the PVC filling strip are 2000 denier bulletproof filaments.

8. The mobile dedicated cable of claim 1, wherein the signal cable layer comprises ten signal lines.

* * * * *